(12) United States Patent
Brewer et al.

(10) Patent No.: US 8,307,829 B2
(45) Date of Patent: Nov. 13, 2012

(54) RESPIRATORY ACCESS ASSEMBLY WITH ROTATING LOCK AND METHOD

(75) Inventors: John Brewer, Marietta, GA (US); Cassandra E. Morris, Roswell, GA (US); Stephen Gianelis, Abington, MA (US); Joe Gordon, Mansfield, MA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 867 days.

(21) Appl. No.: 12/342,846

(22) Filed: Dec. 23, 2008

(65) Prior Publication Data

US 2010/0154799 A1  Jun. 24, 2010

(51) Int. Cl.
*A61M 16/00* (2006.01)
*A62B 9/06* (2006.01)
(52) U.S. Cl. .......... 128/207.14; 128/200.24; 128/205.24
(58) Field of Classification Search .................. 604/317, 604/93.01; 128/200.26, 202.27, 205.24, 128/207.14–207.16
See application file for complete search history.

(56) References Cited

U.S. PATENT DOCUMENTS

| 4,270,778 | A | 6/1981 | Brownell |
| 4,326,520 | A | 4/1982 | Alley |
| 4,569,344 | A | 2/1986 | Palmer |
| 4,641,646 | A | 2/1987 | Schultz et al. |
| 4,836,199 | A | 6/1989 | Palmer |
| 5,158,569 | A | 10/1992 | Strickland et al. |
| 5,377,672 | A | 1/1995 | Kee |
| 5,643,294 | A * | 7/1997 | Tovey et al. .................... 606/148 |
| 5,730,123 | A | 3/1998 | Lorenzen et al. |
| D448,843 | S | 10/2001 | Madsen et al. |
| 6,543,451 | B1 * | 4/2003 | Crump et al. ............ 128/207.14 |
| 6,609,520 | B1 * | 8/2003 | Carlsen et al. ........... 128/207.14 |
| 6,923,184 | B1 | 8/2005 | Russo |
| 7,021,313 | B1 | 4/2006 | Crump et al. |
| 7,353,822 | B2 | 4/2008 | Van Hooser et al. |
| 2004/0221852 | A1 | 11/2004 | Madsen |

FOREIGN PATENT DOCUMENTS

| DE | 29 39 794 A1 | 4/1981 |
| EP | 1 208 865 A2 | 5/2002 |
| GB | 1 443 152 A | 7/1976 |
| GB | 2 061 465 A | 5/1981 |

* cited by examiner

*Primary Examiner* — Melanie Hand
(74) *Attorney, Agent, or Firm* — James B. Robinson; Sue C. Watson

(57) ABSTRACT

A respiratory access assembly includes a movable manifold and a closed suction catheter assembly with a shuttle movable by actuator between the manifold and the closed suction catheter assembly. The assembly includes a flap positioned adjacent the shuttle and the closed suction catheter assembly which is moveable between an open position which permits passage of a suction catheter therethrough and a closed position, which prevents a passage of a suction catheter. The respiratory access assembly permits operable communication with the artificial airway to permit suctioning when in an un-locked position, and prevents the entrance of a suction catheter when in the locked position. A method for using a respiratory access assembly.

8 Claims, 7 Drawing Sheets

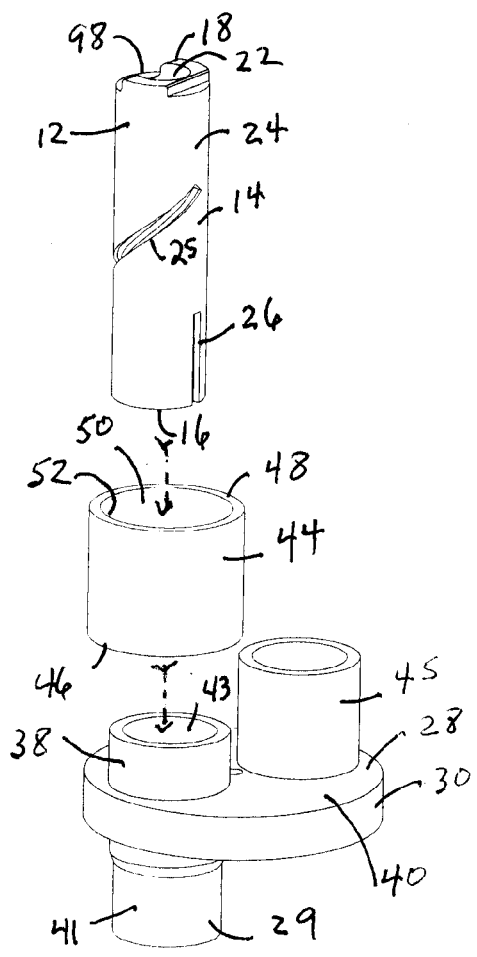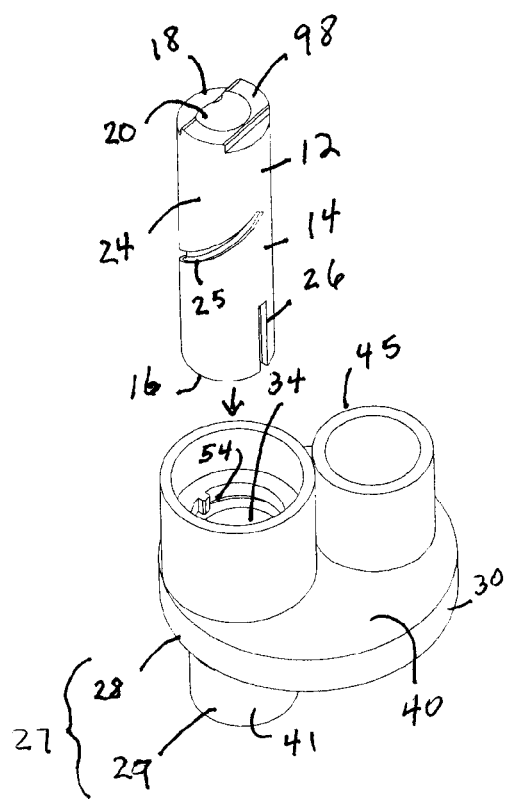
FIG. 3A
FIG. 3B

RESPIRATORY ACCESS ASSEMBLY WITH ROTATING LOCK AND METHOD

BACKGROUND

The inventions disclosed herein relate generally to improved medical care for intubated patients, and more particularly to a novel multiple access respiratory port, assembly, manifold, fitting, adaptor, connector and/or access control assembly inventions, and related methods, for ventilating, aspirating, monitoring, sampling, and providing therapeutic delivery to the respiratory tracts of intubated patients, including infants, adolescents, and adults.

Respiratory patient care is a dynamically developing field in medicine, ranging in its needs from infants to the aged. The range of respiratory ailments, both temporary and permanent, to which such patients are subjected, are many and varied. For example, the range of procedures for intubated patients may include the following: ventilation, aspiration, oxygenation, sampling, visual inspection, in-line sensing, pressure monitoring, flushing, medicating and/or lavage. Most problems now center or focus on multiple needs of the patient and accommodation of multiple treatments, some to be performed at the same time. The lack of equipment to facilely, efficiently, and safely accomplish the multiple therapies in the best interest of the patient has been and continues to be a concern.

For example, in low lung capacity patients, such as premature babies and adults suffering from emphysema, one problem is the removal of accumulated lung secretions. It is undesirable to starve such patients of oxygen during the secretion removal process. Secretion removal is accomplished via a suction catheter which is temporarily positioned via a respiratory access assembly in an artificial airway, i.e., an endotracheal tube placed in a portion of the patient's respiratory tract to provide air (oxygen and other gases) to the lungs of such patients.

With these and other patients undergoing respiratory care while intubated, problems may occur, including problems with a respiratory access assembly. Unsafe extended use of a respiratory access assembly for ventilating, aspirating, suctioning and other functions may result in hospital acquired infections, such as, for example, ventilator acquired pneumonia. Also of concern is the reliability of such respiratory access assemblies. Further, the need to open the ventilator circuit to exchange devices and perform other therapeutic treatments is also a concern.

A respiratory access assembly needs to be quickly and easily removed and exchanged without compromising the quality of health care to the patient. Also of concern with a respiratory access assembly is inadvertent conversion from a closed respiratory system to an open respiratory system via malfunction of a respiratory access assembly. Further, stress to the patient caused by inadvertent partial obstruction or occlusion of air passageways in the closed respiratory system to and from the patient's lungs due to malfunction of a respiratory access assembly is a problem. Moreover, dealing with a large inventory of a variety of incompatible components manufacturered by different manufacturers which may form the respiratory access assembly is also an issue to the health care provider. Therefore, it would be desirable to have an easy to operate, fail-safe, closed-system respiratory access assembly which provides safe and predictable closed-system access to an intubated patient's respiratory system for multiple purposes, and which has safety features to reduce or eliminate inadvertent damage of the closed respiratory system.

The present invention addresses these needs, providing a respiratory access assembly used in a closed system which includes a safety lock. That is, the present invention substantially alleviates problems which occur with present respiratory access assemblies or devices. The present invention operates in a closed ventilating system and accommodates multiple access to the respiratory system of an intubated patient without compromising the closed circuit character of the system and without interruption of the flow of ventilating gases to the patient. Access to the closed respiratory system through one or more access sites is provided, for example, but not by way of limitation, to ventilate the lungs of the patient with gas or gases, to aspirate secretions from the lungs, to oxygenate the lungs to eliminate or reduce residual carbon dioxide therefrom, to visually inspect selected parts of the patient's respiratory system, to sample sputum and gases, to sense parameters such as flow rates, pressure, and/or temperature, to flush with solution(s), and to administer medication, gases, and/or lavage.

SUMMARY OF THE INVENTION

In response to the difficulties and problems discussed herein, a respiratory access assembly is provided. The respiratory access assembly includes a movable manifold having at least one opening. The opening is in communication with an artificial airway of a patient. The assembly also has a closed suction catheter assembly. This assembly comprises at least a connecting end having an opening, a suction catheter, and a sleeve positioned over the suction catheter. The assembly further includes a shuttle which is movable between the opening in the manifold and the opening in the connecting end of the closed suction catheter assembly. The shuttle has an opening formed through it. The shuttle is configured to move into a locked and unlocked position relative to the manifold. In addition, the assembly includes an actuator for moving the shuttle assembly into the locked position and the unlocked position. Finally, the assembly has a flap positioned adjacent the shuttle and the closed suction catheter assembly. The flap is moveable into an opened position permitting operable communication of the suction catheter with the artificial airway when the shuttle is in a locked position. The flap is also moveable into a closed position to prevent operable communication of the suction catheter with the artificial airway when the shuttle is an un-locked position.

In another aspect of the invention, a method of using a respiratory access assembly is provided. The method of using a respiratory access assembly includes providing a respiratory access assembly which has a movable manifold having at least one opening. The opening is in communication with an artificial airway of a patient. The assembly also has a closed suction catheter assembly. This assembly comprises at least a connecting end having an opening, a suction catheter, and a sleeve positioned over the suction catheter. The assembly further includes a shuttle which is movable between the opening in the manifold and the opening in the connecting end of the closed suction catheter assembly. The shuttle has an opening formed through it. The shuttle is configured to move into a locked and unlocked position relative to the manifold. In addition, the assembly includes an actuator for moving the shuttle assembly into the locked position and the unlocked position. Finally, the assembly has a flap positioned adjacent the shuttle and the closed suction catheter assembly. The flap is moveable into an opened position permitting operable communication of the suction catheter with the artificial airway when the shuttle is in a locked position. The flap is also moveable into a closed position to prevent operable communication of the suction catheter with the artificial airway when the shuttle is an un-locked position. The method also includes moving the actuator to simultaneously a) move the shuttle distally to engage and lock to the manifold to permit access through the opening in the manifold and b) move the shuttle away from the end connector of the closed suction catheter assembly such that the flap is positioned in an opened position. The method further includes moving the suction catheter through the end connector, the shuttle, and the manifold such that the suction catheter is positioned in an artificial airway. In addition, the method comprises suctioning secretions from at least a portion of a patient's respiratory tract and artificial airway. Furthermore, the method includes withdrawing the suction catheter from the suction catheter pathway and positioning the suction catheter in its sleeve. Finally, the method includes moving the actuator to move the shuttle proximally to simultaneously a) disengage from the manifold and move into an unlocked position such that the manifold is moveable, and b) move the shuttle toward the end connector of the closed suction catheter assembly such that a portion of the shuttle moves the flap into a closed position thereby blocking and preventing access thereto by the suction catheter.

DEFINITIONS

As used herein the following terms have the specified meanings, unless the context demands a different meaning, or a different meaning is expressed; also, the singular generally includes the plural, and the plural generally includes the singular unless otherwise indicated.

As used herein, the terms "comprise," "comprises," "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof. Similarly, the terms "include", "includes", "including," as well as the terms "has", "have", "having" and derivatives thereof, are intended to be interpreted as the word "comprise", and are intended to be open-ended terms that specify the presence of any stated features, elements, integers, steps, or components, but do not preclude the presence or addition of one or more other features, elements, integers, steps, components, or groups thereof.

As used herein, the term "port" means an opening into or through a component for the passage of an object and/or a liquid and/or a gas.

As used herein, the term "cuff" means a generally cylindrical component having an opening therethrough which is positioned over a port.

As used herein, the phrase "operable communication" means a transmission or passage for a between two points and/or two structures for a specific purpose. In this example, operable communication would be a passage which permits gasses to pass, and may also be configured to permit objects to pass.

As used herein the term "suction catheter" means long, flexible tubes used to remove secretions from the airway and are available in many sizes, commonly from 10 to 20 French and varying lengths, typically from 15 to 25 inches (38 to 64 cm). Suction catheters may be made from latex and other polymers.

Suction catheters are well known and widely commercially available for many medical uses. Suctioning may be performed using an "open" or "closed" system. In the open system, the suction catheter is merely a flexible plastic tube that is inserted into the flexible lumen with a source of suction connected to the proximal end of the suction catheter. Anything that the suction catheter touches before entering the lumen must be maintained in a sterile condition so a "sterile field" must be created on or next to the patient. The suction catheter must be carefully handled after it is used since it will be coated with the patient's secretions. In contrast, in the "closed" system, for example that disclosed in commonly owned U.S. Pat. No. 4,569,344, a device which may be used to suction secretions is enclosed within a generally cylindrical plastic bag to eliminate or minimize contamination of the suction catheter prior to use. This is generally referred to as a "closed suction catheter" and is available under the tradename TRACH CARE® from BALLARD® Medical Products (Kimberly-Clark Corporation). As the patient requires artificial removal of secretions, the suction catheter may be advanced through one end of the plastic bag, through a connecting fitting and into the flexible lumen. The other, proximal end of the suction catheter is attached to a source of suction. Suction may be applied using, for example, a finger controlled valve on the proximal end of the suction catheter, and the secretions removed. Secretions are thus drawn into the lumen of the suction catheter tube and removed and the system remains closed. The suction catheter is subsequently withdrawn from the flexile lumen and back into the plastic bag to keep the circuit closed. Closed suction systems are generally preferred by healthcare providers since the provider is better protected from the patient's secretions. Closed suction systems are also easier and quicker to use since a sterile field need not be created each time the patient must be suctioned, as is required in open suction systems. The closed suction catheter may be permanently attached to the proximal end of the flexible lumen or may be detachably connected so that it may be replaced periodically.

As used herein, the phrase "suction catheter pathway" includes the components defined herein which are or may be coupled to a suction catheter assembly which, when aligned, provide an opening in an axial alignment to permit a suction catheter to be moved therethrough.

As used herein, the term "couple" includes, but is not limited to, joining, connecting, fastening, linking, tying, adhering (via an adhesive), or associating two things integrally or interstitially together.

As used herein, the term "configure" or "configuration", and derivatives thereof means to design, arrange, set up, or shape with a view to specific applications or uses. For example: a military vehicle that was configured for rough terrain; configured the computer by setting the system's parameters.

As used herein, the terms "substantial" or "substantially" refer to something which is done to a great extent or degree; a significant or great amount; for example, as used herein "substantially" as applied to "substantially" covered means that a thing is at least 70% covered.

As used herein, the term "alignment" refers to the spatial property possessed by an arrangement or position of things in a straight line.

As used herein, the terms "orientation" or "position" used interchangeably herein refer to the spatial property of a place where or way in which something is situated; for example, "the position of the hands on the clock."

As used herein, the term "about" adjacent to a stated number refers to an amount that is plus or minus ten (10) percent of the stated number.

These terms may be defined with additional language in the remaining portions of the specification.

BRIEF DESCRIPTION OF THE DRAWINGS

FIG. 3A is a partially exploded perspective view of the two-part base manifold, the distal connector and the shuttle of FIG. 2, showing the position of the shuttle and distal connector relative to the two-part base manifold;

FIG. 3B is a partially exploded perspective view of the two-part base manifold, the distal connector and the shuttle of FIG. 2, but showing the distal connector in its position connected to the two-part base;

DETAILED DESCRIPTION OF THE INVENTION

Figure 1:
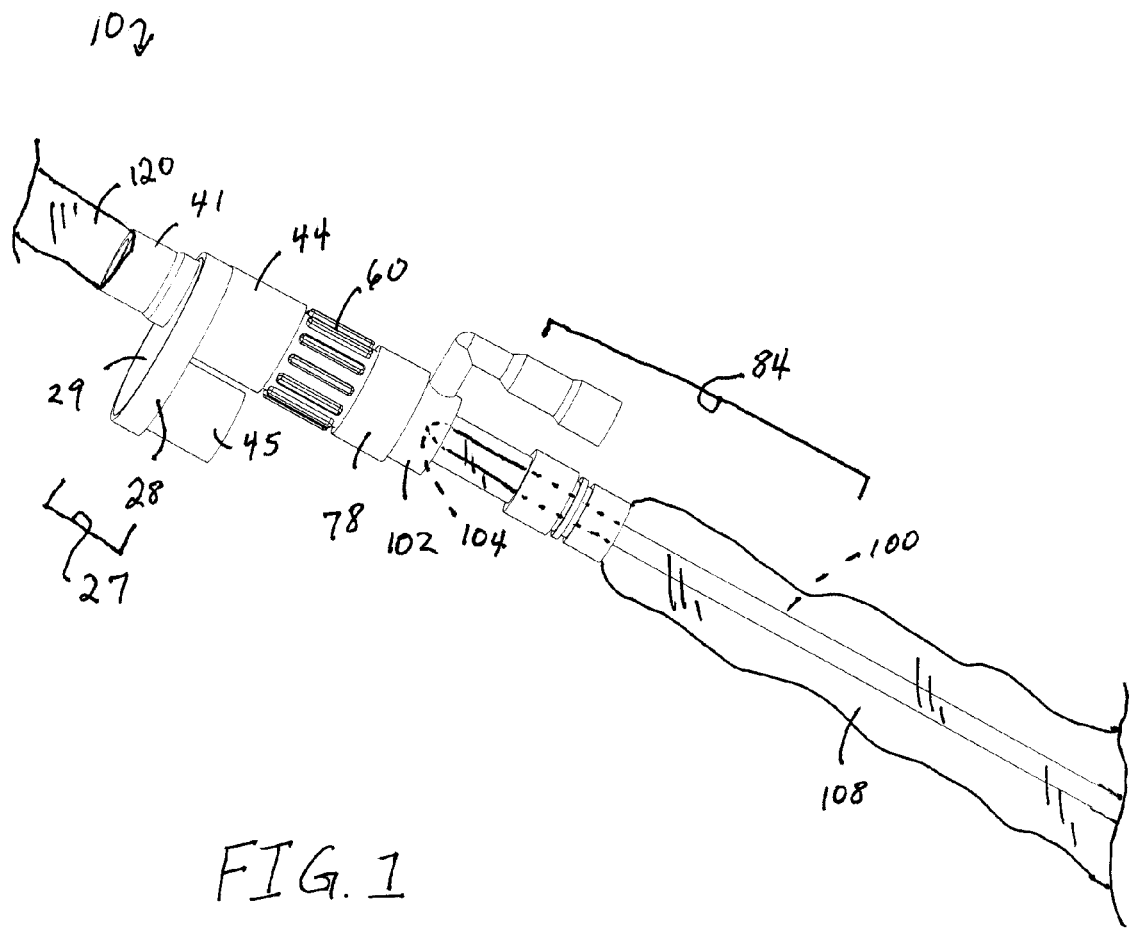
FIG. 1 is a perspective view of the respiratory access assembly of the present invention releaseably coupled to a suction catheter assembly.

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Current designs for respiratory access assemblies may have only one port. In these instances, the suction catheter must be removed when other tasks need to be performed, such as, for example, bronchoscopy, bronchial alveolar lavage, and so forth. Opening a closed ventilating system by removing the suction catheter on such a ventilated patient can lead to infection, as noted previously. Also, current designs of multiple access port manifolds and/or assemblies do not contain a safety lock. In certain instances, due to the lack of such a safety lock, the introduction of a suction catheter through a manifold port may result in a portion of the catheter being guillotined or cut off and aspirated into the patient's lungs. This can lead to significant complications, including airway blockage, infection, and even death. Further, failure to adequately seal a respiratory access assembly may cause a compromise of positive end-expiration pressure (PEEP), which may in turn may cause suboptimal ventilation which can result in collapsing alveoli in the patient's lungs. The present invention describes a respiratory access assembly which includes features which permits multiple access without opening the closed ventilation system, and it contains a safety lock feature which prevents loss of any portion of the suction catheter.

Figure 2:
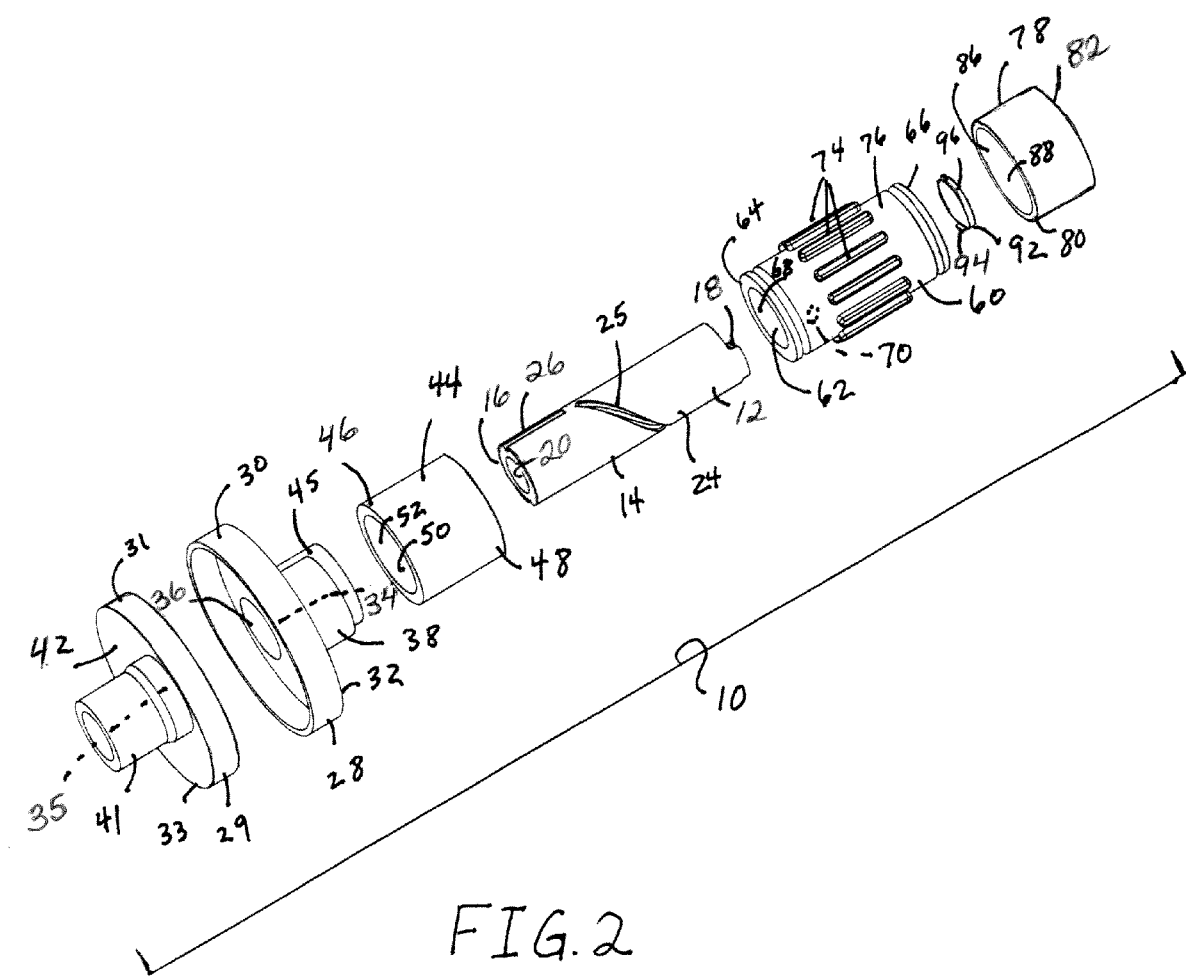
FIG. 2 is an exploded perspective view of the components of the respiratory access assembly of FIG. 1 but without the suction catheter assembly, and showing in axial alignment a two-part base manifold, a distal connector, the shuttle, a rotator, a movable door or lock (positioned in a closed position), and a proximal connector.

Turning now to the drawings, as illustrated in FIGS. 1-7, a respiratory access assembly 10 is provided. The assembly 10, as shown in FIGS. 1 and 2, includes a shuttle 12 which has a generally cylindrical body 14 having opposed first or distal and second or proximal ends 16, 18. An opening 20 is formed through the cylindrical body 14 from the first end or distal end 16 and extending through the second end or proximal end 18, thereby providing an inner surface 22 having an inner diameter. An outer surface 24 of the shuttle 12 has a first groove 25 formed in the cylindrical body 14. The first groove 25 is desirably, but not by way of limitation, formed in a winding pattern about at least a portion of the outer surface 24. The distal end 16 also may have one, or desirably a pair of end grooves (collectively "26") formed in the outer surface 24 starting at the distal end 16 and extending a distance toward the proximal end 18. The end grooves 26 may, but not by way of limitation, be configured as straight grooves generally aligned axially relative to the shuttle 12. The distal end 16 is desirably positioned adjacent a two-part manifold 27 having a proximal base 28 and a distal base 29, respectively, which cooperate to provide the manifold 27.

The proximal base 28 and the distal base 29 of the manifold 27 are each desirably, but not by way of limitation, disk-shaped, as illustrated in FIGS. 2 and 3A-3B. The proximal and distal bases 28, 29 may each have a lip 30, 31 formed at an outer edge 32, 33 of each base 28, 29, respectively. The proximal and distal bases 28, 29 each desirably may also have at least one or a first opening 34, 35, respectively, formed therethrough. In addition, the proximal base 28 desirably may also have another or a second opening 36 formed therethrough, and it will be understood that additional openings (not shown) may also be provided. The proximal base 28 desirably includes a cylindrical locking cuff 38 formed about a perimeter of the first opening 34 on a proximal surface 40 of the proximal base 28. The distal base 29 may also have a cylindrical cuff 41 formed about a first opening 35 on a distal surface 42 of the distal base 29.

The proximal base 28 also may include a second cuff 45 formed about a perimeter of the second opening 36 on the proximal surface 40 of the base 28. The locking cuff 38 includes an inner surface 43 having an inner diameter sized to receive the distal end 16 of the shuttle 12.

The proximal and distal bases 28, 29 of the manifold 27 are cooperatively coupled together, by any means known in the art. In addition, they may include a rotating pin (not shown) positioned axially through each base 28, 29 which permits them to rotate relative to each other. For the purposes described herein, it will be appreciated that the locking cuff 38 of the proximal base 28 and the cuff 41 of the distal base 29 are desirably maintained in an axial alignment. The cuff 41 of the distal base 29 is desirably coupled to or in communication with an artificial airway 120 positioned in at least a portion of a patient's respiratory system.

When the distal end 16 of the shuttle 12 is moved away from the locking cuff 38 of the proximal base 28, the proximal and distal bases 28, 29 are configured to move or rotate relative to each other, to permit access to the second cuff 41. However, when the distal end 16 of the shuttle 12 is moved into the locking cuff 38, the manifold bases 28, 29 are locked into a fixed, non-rotating position. The proximal and distal bases 28, 29 of the manifold 27 are positioned and held adjacent to the distal end 16 of the shuttle 12 by a cylindrical distal connector 44.

Figure 4:
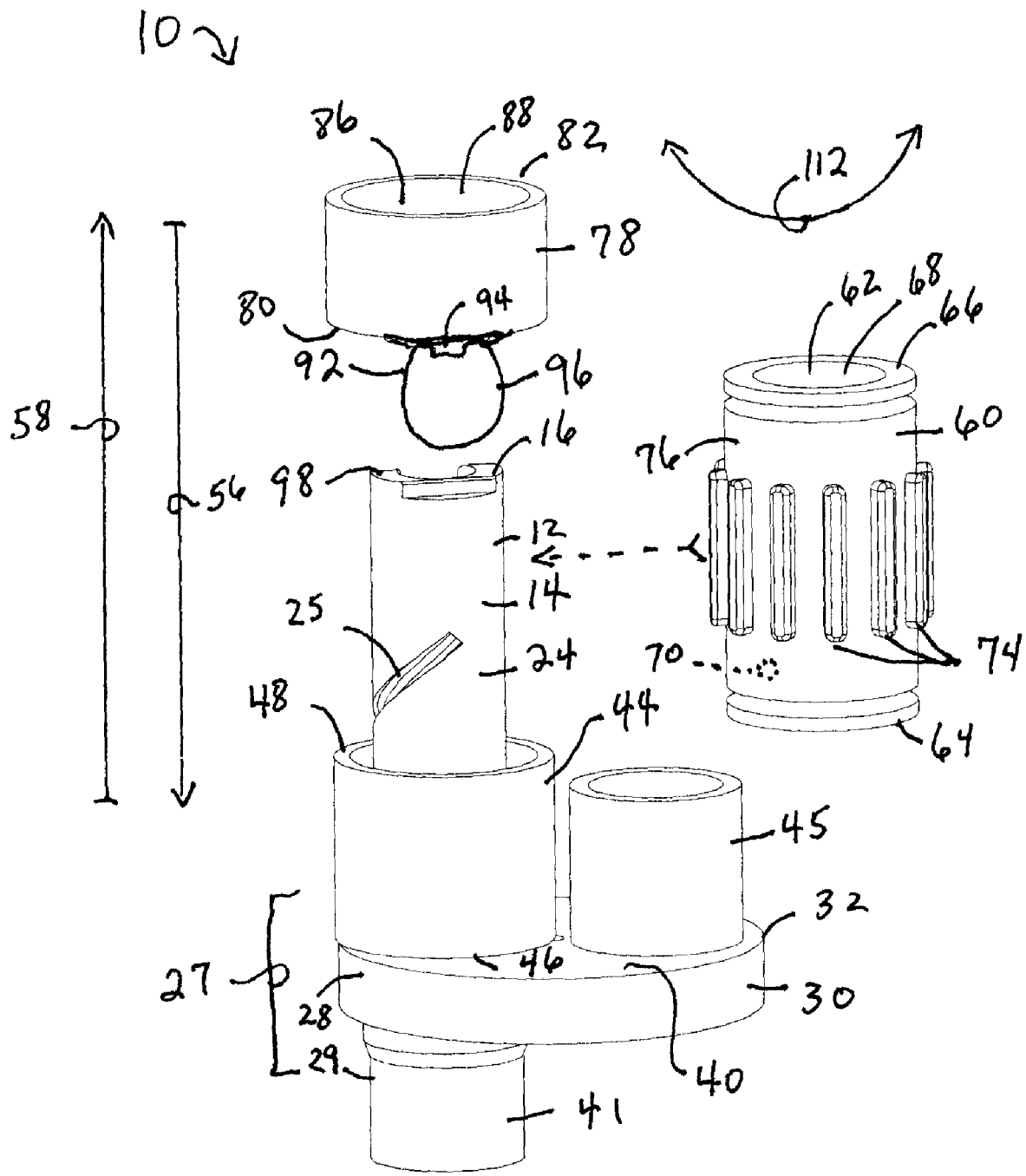
FIG. 4 is a partially exploded perspective view of the shuttle in a non-coupled position relative to the distal connector and two-part base, the door positioned in an opened position relative to the proximal connector and the shuttle, the rotator positioned to the side for illustration purposes only to better show operational positions of the shuttle position.
Figure 5:
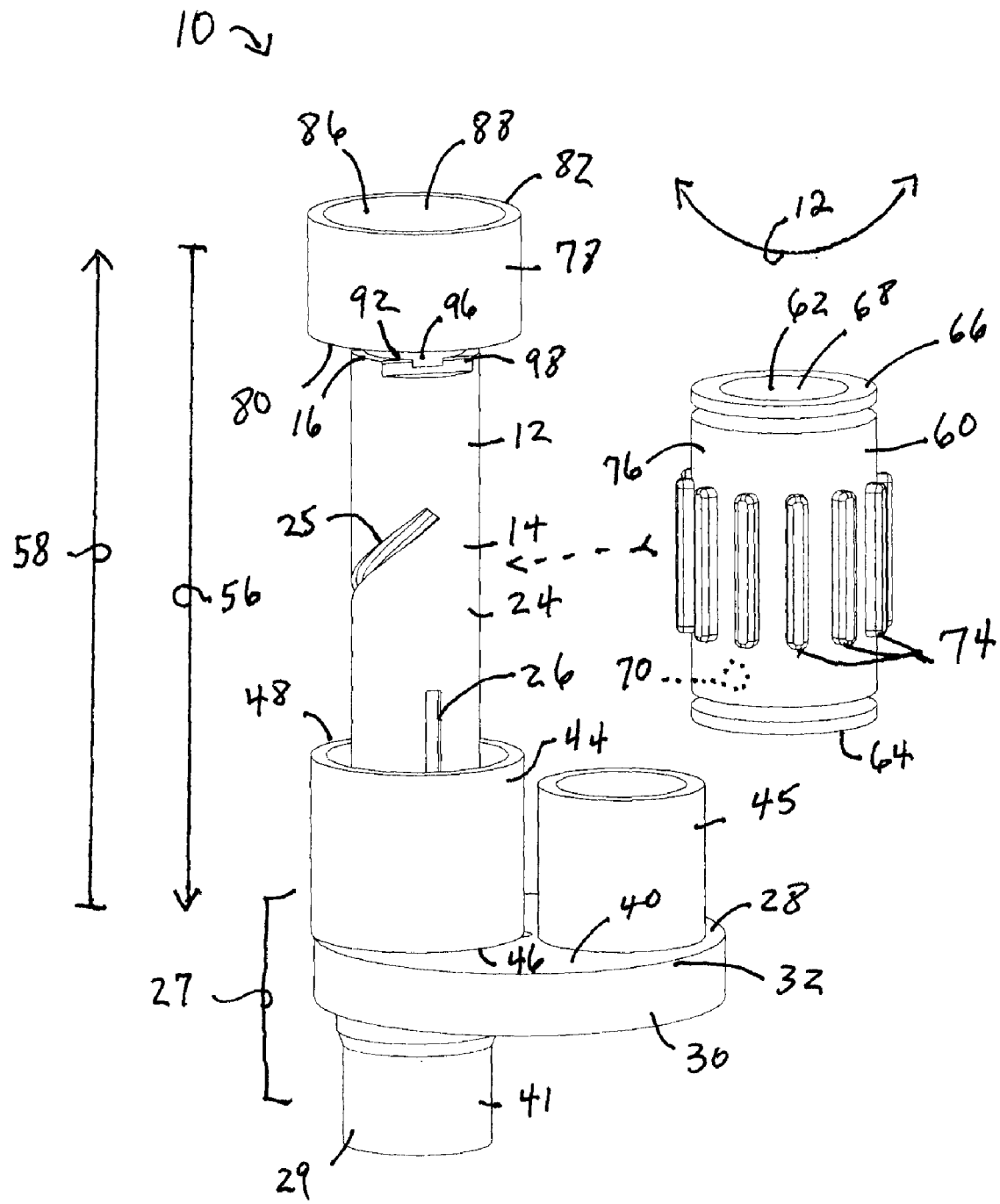
FIG. 5 is a partially exploded perspective view of the shuttle in a non-coupled position relative to the distal connector and two-part base, the door positioned in a closed, locked position relative to the proximal connector and the shuttle, the rotator positioned to the side for illustration purposes only to better show operational positions of the shuttle position.

The distal connector 44, as illustrated in FIGS. 2-6, includes a distal portion 46 which is positioned over a portion of the outer surface 24 of the distal end 16 of the shuttle 12. The distal connector 44 also includes a proximal portion 48 which is positioned over a portion of the locking cuff 38 of the proximal base 28 of the manifold 27. The distal connector 44 includes an opening 50 extending from the distal portion 46 through the proximal portion 48 which is configured to have an inner surface 52 and an inner diameter. The distal connector 44 permits the distal end 16 of the shuttle 12 to move axially therein (FIGS. 4 and 5). The inner surface 52 of the distal connector 44 also desirably includes a pair of pins 54 (only one of the pair illustrated in FIG. 3B). Each pin 54 is configured to engage the one of the end grooves 26 of the distal end 16 when it is positioned within the distal connector 44, thereby locking the shuttle 12 into a fixed, non-rotatable position. At the same time, the distal portion 46 of the distal connector 44 is moved generally an a distal direction 56 so that the distal portion 46 is positioned in the locking cuff 38, thereby locking the proximal base 28 and the manifold 27 in a fixed, unmoving, locked position. When the distal end 16 of the shuttle 12 is moved in a proximal direction 58, the distal end 16 and the end grooves 26 therein move away from the pins 54 and becomes unlocked from the distal connector 44, while the distal connector 44 moves in the proximal direction 58 as well relative to the proximal base 28 of the manifold 27, so that the proximal base 28 is again rotatable in its unlocked position.

Figure 6:
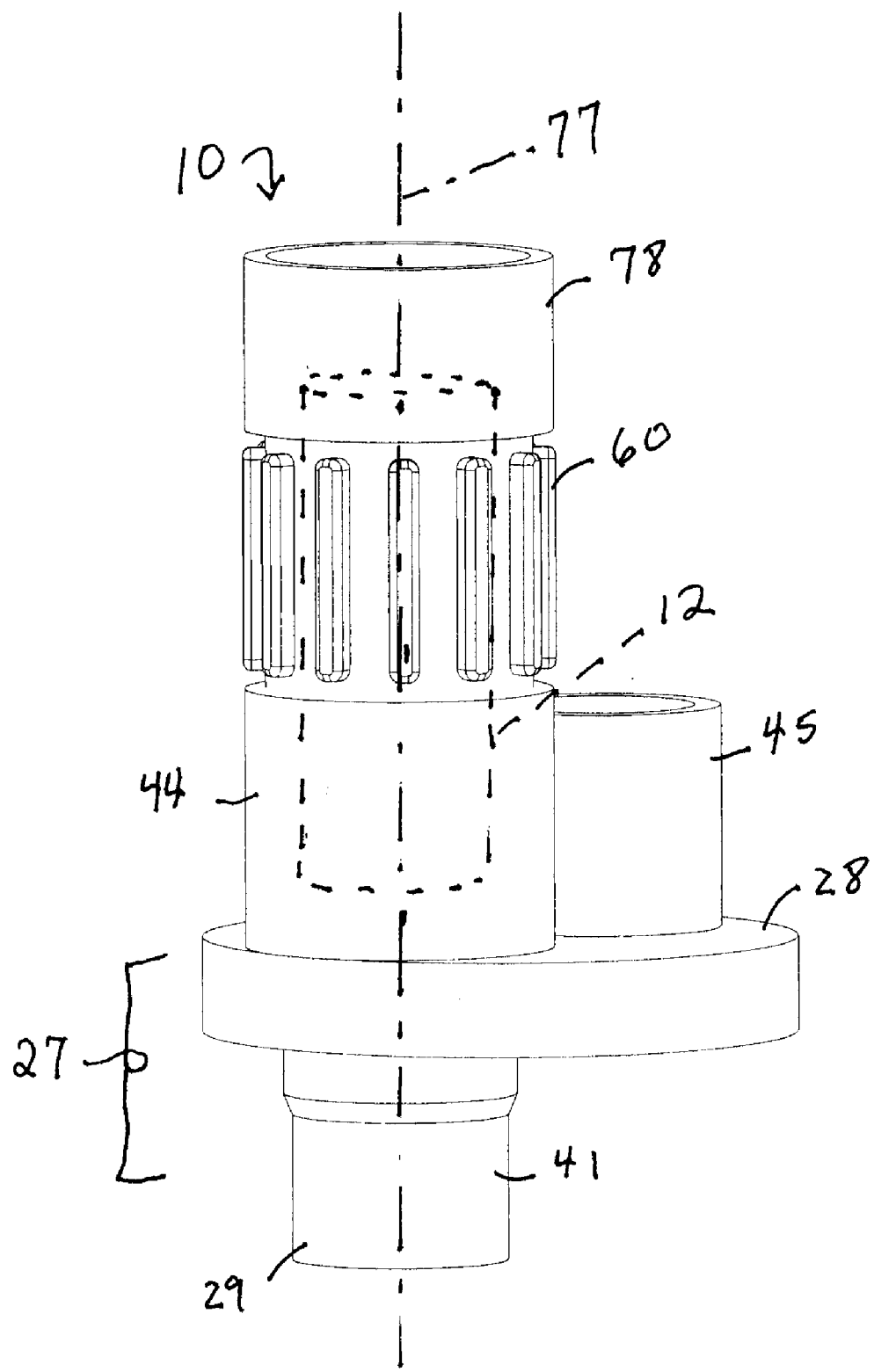
FIG. 6 is a perspective view of the respiratory access assembly, showing the shuttle via phantom lines.
Figure 7:
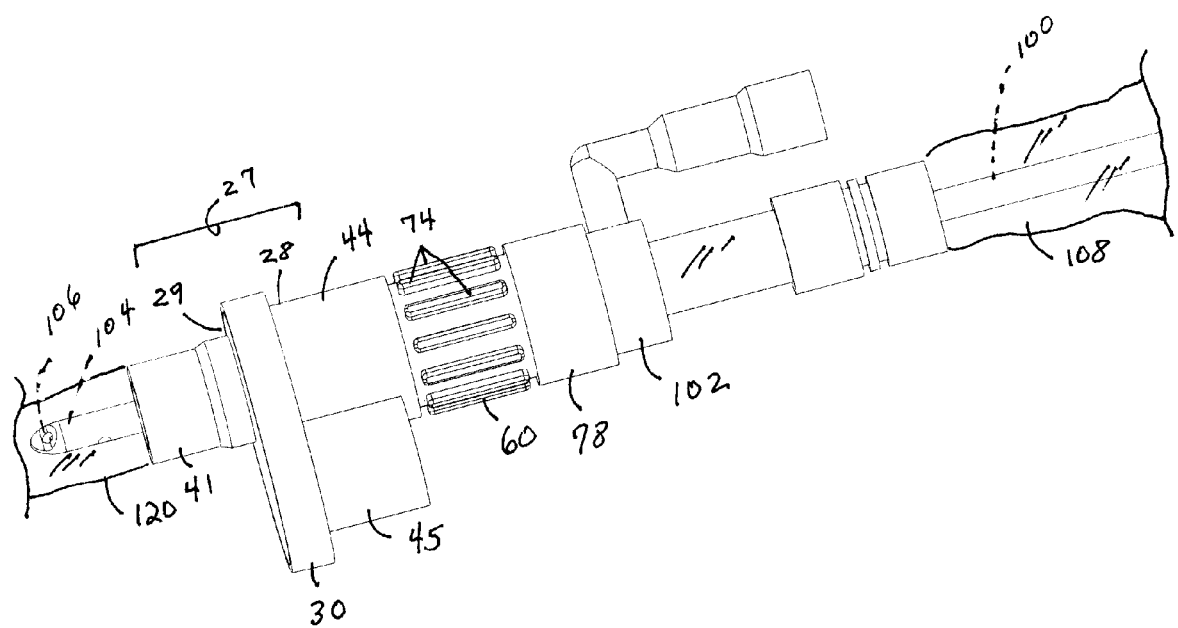
FIG. 7 is a perspective view of the respiratory access assembly of FIG. 1, but showing a suction catheter of the suction catheter assembly positioned therethrough.

An actuator or rotator 60 is desirably movably positioned over the shuttle 12 (FIG. 6). The actuator or rotator or rotating lock 60 is desirably cylindrically shaped, and has an opening 62 formed through opposing distal and proximal ends 64, 66. The opening 62 forms an inner surface 68 of the rotator 60, which has an inner diameter configured to be slightly larger than an outer diameter of the shuttle 12, and therefore accommodates the shuttle 12 and movement thereof. The rotator 60 desirably has a pin 70 provided on the inner surface 68, which is configured to fit into the first groove 25 on the outer surface 24 of the shuttle 12. The rotator 60 also may include a plurality of ribs 74 (collectively "74") on an outer surface 76 thereof, so that a user may grasp the outer surface 76 and rotate the rotator 60. When rotated in this manner, the rotator 60 is configured to move the shuttle 12 in the distal or proximal directions 56, 58 on a longitudinal axis 77. That is, when the rotator 60 is grasped by a user and rotated, the pin 70 on the inner surface 68 of the rotator 60 engages the first groove 25 on the outer surface of the shuttle 12 to move the shuttle distally, toward the proximal base 28 of the manifold 27 or, alternatively, proximally, toward a cylindrical proximal connector 78.

The proximal connector 78, as illustrated in FIGS. 4-7, includes a distal portion 80 which is positioned over a portion of the outer surface 24 of the proximal end 18 of the shuttle 12. The proximal connector 48 also includes a proximal portion 82 which desirably maybe connected to at least a portion of a suction catheter assembly 84. The proximal connector 78 includes an opening 86 extending from the distal portion 80 through the proximal portion 82 which is configured to provide an inner surface 88 and an inner diameter. The proximal connector 78 cooperates with the distal connector 44 and the rotator 60 as well as with the shuttle 12 to permit the shuttle 12 to rotate or move axially along the longitudinal axis 77. The opening 34 in the proximal base 28, the opening 20 in the shuttle 12 and the openings 50, 86 in the distal and proximal connectors 44, 78, respectively, provide a suction catheter pathway 90 through which the suction catheter can be passed through in order to suction secretions from a patient's artificial airway and/or respiratory tract.

The distal portion 80 of the proximal connector 78 desirably includes a flapper valve 92. The flapper valve 92 may include a mount 94 and a door, flap or lock 96 which is pivotably coupled to the mount 94. The door, flap or lock 96 of the flapper valve 92 is desirably biased so that the door, flap, or lock 96 extends distally away from the mount 94. That is, the door, flap, or lock 96, when open, may be positioned in a generally parallel alignment relative to the longitudinal axis 77, when the shuttle 12 is positioned distally toward the manifold 27. However, when the shuttle 12 is moved via the rotator 60 toward the proximal connector 78, an edge 98 of the second end or proximal end 18 of the shuttle 12 contacts the flap 96 and moves the flap 96 such that it is positioned transversely across the opening 20 in the shuttle 12, or, alternatively, across the opening 86 in the proximal connector 78, thereby blocking the opening 20 and/or the opening 86. The movement of the shuttle 12 relative to the flapper valve 92 in the proximal connector 78 therefore affects whether the opening 20 through the shuttle 12 and/or the opening 86 in the proximal connector 78 remains open, or whether the opening(s) is/are blocked by the flap 96 of the flapper valve 92.

Therefore, when the rotator 60 is rotated such that the shuttle 12 is moved in the distal direction 56 toward the distal connector 44 and positioned in a locked position relative thereto (FIG. 4), the opening 20 through the shuttle 12 and/or the opening 86 through the proximal connector 78 remains in an open condition because the proximal end 18 of the shuttle 12 has been moved away from the flapper valve 92 such that the flap 96 is biased in a distal direction 56, away from the mount 94. When the rotator 60 is rotated such that the shuttle 12 is moved in the proximal direction 58 toward the proximal connector 78 and positioned in an unlocked position relative thereto, a position which permits the proximal base 28 of the manifold 27 to rotate, the flap 96 on the flapper valve 92 is moved by the edge 98 of the proximal end 18 of the shuttle 12 in the proximal direction 58 until the flap 96 is positioned transversely across the opening 20 of the shuttle 12 and/or the opening 86 in the proximal connector 78 thereby effectively blocking and closing the opening 20 and/or 86 in a closed position (FIG. 5). In this closed position, no object, including a suction catheter 100 of the suction catheter assembly 84 is movable through the opening 20 and/or 86.

Alternatively, however, the flapper valve 92 may be positioned on a distal end 16 of the shuttle 12, and the flap 96 is biased so that in an open position, the flap 96 extends proximally, toward the proximal connector 78, and parallel to the longitudinal axis 77. Therefore, when the shuttle 12 is moved in the distal direction 56 and coupled to the locking cuff 38, the flap 96 is open. When the shuttle 12 is moved or rotated in the proximal direction 58 into an un-locked position relative to the locking cuff 38, the flap 96 moves against a collar (not shown) provided on the inner surface 88 of the proximal connector 78. As the shuttle 12 moves proximally, the flap 96 contacts the collar and the collar urges the flap 96 into a transverse position relative to the longitudinal axis 77 and the collar holds the flap in the transverse position until the shuttle 12 and therefore the flapper valve 92 is moved away from it (not shown).

The suction catheter assembly 84 includes at least a distal coupler 102 (FIGS. 1 and 7) which releaseably couples to the proximal portion 82 of the proximal connector 78. The suction catheter 100 also includes a distal tip 104 with at least one opening 106 therein, as well as a sleeve 108 which extends from the distal coupler 102 to a proximal coupler (not shown) to substantially cover the suction catheter 100. The proximal coupler desirably is adapted to couple to at least a portion of a suctioning apparatus (not shown). The suction catheter 100 has a length which is sufficient to extend through the respiratory access assembly 10 and through an attached artificial airway 120 and into a portion of a patient's respiratory tract to suction secretions therefrom. When suction is discontinued and the suction catheter 100 is withdrawn, the length of the suction catheter 100 is contained within the sleeve 108 and is therefore positioned outside of the closed circuit ventilation system of the patient until needed for suctioning again.

In a method of use of the respiratory access assembly 10, as illustrated in FIGS. 1 and 4-7, the distal connector 44, the rotator 60 and the proximal connector 78 are positioned at least partially over the shuttle 12. The distal connector is in contact with at least a portion of the locking cuff 38 of the proximal base 28 of the manifold 27. When the suction catheter 100 is not in use, it is maintained in its position in its sleeve 108 between the distal and proximal couplers of the suction catheter assembly 84. To use the suction catheter 100, i.e., to extend the suction catheter 100 through the suction catheter pathway 90, the rotator is manually actuated or rotated by a user in one of two rotating directions 112 so that the shuttle 12 is moved in a distal direction 56. When the rotator is manually rotated, the pin 70 on the rotator 60 engages the first groove 25 on the outer surface 24 of the shuttle 12 in order to cause the shuttle 12 to rotate in the distal direction 56. The distal end 16 of the shuttle is positioned in the distal connector 44 and the pins 54 on the inner surface 52 of the distal connector engages the end grooves 26 of the shuttle and locks the shuttle 12 to the distal connector 44, thereby moving the distal end 16 of the shuttle 12 into the locking cuff 38 of the proximal base 28 of the manifold, and locking the base 28 and manifold 27 in a fixed and non-movable, locked position. Simultaneously, the proximal end 18 of the shuttle 12 is moved away from the proximal connector 78 and the flapper valve 92, thereby permitting the door or flap 96 to move in its biased direction, i.e., the distal direction 56 within the opening 20 and/or 86 of the shuttle 12 and/or the proximal connector 78, respectively. The position of the flap 96 provides a substantial opening through the opening(s) 86 and/or 20. The distal end 16 is also positioned in a locked position with respect to the first opening 34 and the locking cuff 38. Therefore, in the locked position, the suction catheter pathway 90 is open to permit passage of the suction catheter 100 therethrough.

It will be appreciated that it is impossible to guillotine or cut any portion of the suction catheter 100 within the assembly 10, should the suction catheter 100 be only partially or incompletely withdrawn from the suction catheter pathway 90. This is because the shuttle 12 will not rotate into another position when the flap 96 of the flapper valve 92 blocks its movement.

When suctioning is completed, the suction catheter 100 is desirably withdrawn completely to its sleeve 108. To maintain the suction catheter 100 in its position within its sleeve 108, the rotator 60 is again manually grasped and moved in the proximal direction 58. In this manner, the pins 54 in the distal connector 44 disengages with the end grooves 26 in the distal end 16 of the shuttle 12 and the distal end 16 moves within the distal connector 44 and away from the locking cuff 38, thereby releasing the proximal base 28 or the manifold 27 from its locked position and moving it into an unlocked position, whereby the proximal and distal base 28, 29 of the manifold 27 may rotate relative to each other, so that the second opening 36 in the proximal base 28 may be used for bronchoscopy, and the like. The rotator 60 then engages the shuttle 12 via the pin 70 in the first groove 25 as previously described herein to move the shuttle 12 axially and in the proximal direction 58. Therefore, the proximal end 18 of the shuttle 12 is moved toward the proximal connector 78. When the edge 98 of the proximal end 18 of the shuttle 12 contacts the flap 96 of the flapper valve 92, the edge 98 urges the flap 96 to move until the flap is positioned in a transverse or closed position across the opening 20 and/or 86 of the shuttle 12 and/or the proximal connector 78. This position of the flap 96 of the flapper valve 92 effectively blocks the opening 20 and/or 86 and prevents the introduction of the suction catheter 100 into the suction catheter passageway 90.

It will be understood that the distal and proximal connectors 44, 78 and the rotator 60, as well as any other components herein, are moveably coupled together by any means which permits the components to operate as shown and/or described herein. The flap may be formed from a polymer material, and the spring in the flapper valve 96 may desirably be metal, plastic, or a combination thereof. The components of the assembly may also be formed from a polymer material, and desirably, but not by way of limitation, are formed from a polycarbonate, acrylic, and so forth.

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A respiratory access assembly, comprising:
a movable manifold having at least one opening, the opening in communication with an artificial airway of a patient;
a closed suction catheter assembly comprising at least a connecting end having an opening formed therethrough, a suction catheter, and a sleeve positioned over the suction catheter;
a flap positioned adjacent the closed suction catheter assembly, the flap movable into an opened position permitting passage of the suction catheter into the artificial airway and the flap movable into a closed position that does not permit passage of the suction catheter into the artificial airway;
a shuttle movable between the opening in the manifold and the opening in the connecting end of the closed suction catheter assembly, the shuttle having an opening to permit passage of the suction catheter therethrough, said shuttle configured to move into a locked and unlocked position relative to the manifold;
an actuator for moving the shuttle assembly into the locked position and the unlocked position, wherein the actuator is a rotator which is positioned over at least a portion of the shuttle and is movably coupled thereto;
wherein said locked position prevents movement of said manifold and permits opening of said flap and wherein said unlocked position allows movement of said manifold and prevents opening of said flap; and
wherein the shuttle includes a first groove and the rotator includes a pin which engages the first groove to move the shuttle upon rotation of the rotator.

2. The respiratory access assembly of claim 1, further comprising a distal connector positioned at least partially over the cuff of the manifold and a distal end of the shuttle.

3. The respiratory access assembly of claim 2, wherein the shuttle includes end grooves and the distal connector includes pins which engage the end grooves to move the shuttle and the manifold into a locked position relative to each other.

4. A respiratory access assembly, comprising:
   a movable manifold having at least one opening, the opening in communication with an artificial airway of a patient;
   a closed suction catheter assembly comprising at least a connecting end having an opening formed therethrough, a suction catheter, and a sleeve positioned over the suction catheter;
   a flap positioned adjacent the closed suction catheter assembly, the flap movable into an opened position permitting passage of the suction catheter into the artificial airway and the flap movable into a closed position that does not permit passage of the suction catheter into the artificial airway;
   a shuttle movable between the opening in the manifold and the opening in the connecting end of the closed suction catheter assembly, the shuttle having an opening to permit passage of the suction catheter therethrough, said shuttle configured to move into a locked and unlocked position relative to the manifold;
   an actuator for moving the shuttle assembly into the locked position and the unlocked position;
   wherein said locked position prevents movement of said manifold and permits opening of said flap and wherein said unlocked position allows movement of said manifold and prevents opening of said flap; and
   a proximal connector which is positioned over a portion of the shuttle, wherein at least a portion of the flap is positioned within the proximal connector.

5. The respiratory access assembly of claim 4, wherein the portion of the shuttle moves the flap against a portion of the proximal connector in order to position the flap across the opening of the shuttle.

6. A method of using a respiratory access assembly, comprising:
   a providing a respiratory access assembly comprising
   a movable manifold having at least one opening, the opening in communication with an artificial airway of a patient;
   a closed suction catheter assembly comprising at least a connecting end having an opening formed therethrough, a suction catheter, and a sleeve positioned over the suction catheter;
   a shuttle movable between the opening in the manifold and the opening in the connecting end of the closed suction catheter assembly, the shuttle having an opening therethrough and configured to move into a locked and unlocked position relative to the manifold;
   an actuator for moving the shuttle assembly into the coupled and released position; and
   a flap positioned adjacent the shuttle and the closed suction catheter assembly, the flap movable into an opened position permitting passage of the suction catheter into an artificial airway when the shuttle is in a locked position, and the flap movable into a closed position preventing passage of the suction catheter through the shuttle when the shuttle is an un-locked position;
   moving the actuator to simultaneously a) move the shuttle distally to engage and lock to the manifold to permit access through the opening in the manifold and b) move the shuttle away from the end connector of the closed suction catheter assembly such that the flap is positioned in an opened position;
   moving the suction catheter through the end connector, the shuttle, and the manifold such that the suction catheter is positioned in an artificial airway;
   suctioning secretions from at least a portion of a patient's respiratory tract and artificial airway;
   withdrawing the suction catheter from the suction catheter pathway and positioning the suction catheter in its sleeve;
   moving the actuator to move the shuttle proximally to simultaneously a) disengage from the manifold and move into an unlocked position such that the manifold is movable, and b) move the shuttle toward the end connector of the closed suction catheter assembly such that a portion of the shuttle moves the flap into a closed position thereby blocking and preventing access thereto by the suction catheter.

7. The method of claim 6, wherein in the step of moving the actuator to move the shuttle distally, the step includes rotating the actuator.

8. The method of claim 6, wherein in the step of moving the actuator to move the shuttle proximally, the step includes rotating the actuator.

* * * * *